United States Patent [19]

Robins

[11] 4,383,526

[45] May 17, 1983

[54] DISPOSABLE TRACTION SPLINT

[76] Inventor: Seymour Robins, 50 E. Sheffield Rd., Sheffield, Mass. 01257

[21] Appl. No.: 260,894

[22] Filed: May 6, 1981

[51] Int. Cl.³ .............................................. A61F 5/04
[52] U.S. Cl. ..................................... 128/87 R; 128/93
[58] Field of Search .................. 128/87 R, 84 R, 84 C, 128/83, 86, 85, 93

[56] References Cited

U.S. PATENT DOCUMENTS

| | | | |
|---|---|---|---|
| 2,141,100 | 12/1938 | Warden | 128/87 R X |
| 2,384,779 | 9/1945 | Williams | 128/84 R |
| 2,409,195 | 10/1946 | Crawford | 128/87 R |
| 2,700,383 | 1/1955 | Moodie | 128/87 R |
| 4,209,011 | 6/1980 | Peck et al. | 128/93 X |

*Primary Examiner*—John D. Yasko
*Attorney, Agent, or Firm*—Ross, Ross & Flavin

[57] ABSTRACT

Fractures of the extremities require appropriate splinting and it is recognized that splinting should be applied at the scene of the injury before the patient is moved. Ergo the emergency traction splint hereof as a part of first aid equipment which may be readily assembled into operating position at the site of an accident for first echelon service while the injured person is removed from the scene and brought with injured limb in traction to a hospital for treatment at a higher echelon, which splint may be readily disposed of, once it has served its emergency purpose. The splint serves to hold longitudinal traction on a broken femur or a hip dislocation. That is, it has a capacity for obtaining and holding a pulling action on the injured leg.

4 Claims, 10 Drawing Figures

DISPOSABLE TRACTION SPLINT

This invention relates to an emergency traction splint as a part of first aid equipment which may be readily assembled into operating position at the site of an accident for first echelon service while the injured person is removed from the scene and brought with injured limb in traction to a hospital for treatment at a higher echelon and which may be readily disposed of, once it has served its emergency purpose.

The problems inherent at the scene of an accident in attending to a person suffering an injured limb can be readily appreciated and the need for an emergency splint to aid in the placement of the injured limb in traction at the earliest possible moment is obvious.

The primary object of the invention is to provide a traction splint for use as soon as it could be applied to a fractured femur and held in place until the orthopedic surgeon could take corrective measures. The time consumed might range anywhere from five minutes to five hours.

At the scene of an accident, the governing rule is, if one has reason to suspect a fracture, to treat for a fracture. It isn't essential for one to see a bone sticking out or in disposition at an obviously incorrect angle. There are signs which suggest a possible fracture or dislocation, and those signs, if present, are enough to justify treatment accordingly.

Very specifically, the invention provides a means for obtaining and holding a longitudinal pulling action on the injured leg.

One salient point must be made ab initio. It relates to the real life-threatening urgency of having traction applied to the injured leg. Minutes are important. A fracture of the thighbone can be extremely painful, not to mention dangerous. The femur is the largest bone in the body and is surrounded by very powerful muscles and ligaments. At the time of fracture, the tendency of those muscles is to pull the broken bone sections together, or worse toward and then past each other. The movement of these broken parts against each other is incredibly painful, but worse, the broken parts have the capacity for cutting through arteries, veins and nerves. Extreme bleeding can result; shock inevitably follows.

The splint is extremely stable and will hold the injured limb absolutely immobile whether in the field or in a moving vehicle. The splint is constructed without moving parts, requires no special expertise in its use, and may be packaged in a small volume as part of a first aid kit. With appropriate selection of strong but lightweight cardboard, the splint may even be economically disposable after a single use. It satisfies the real tangible need for a traction splint which is inexpensive and within the budget possibilities of the organizations most needing same, that is organizations of the first responder type which usually do not have the means, economic or otherwise, for having available the more expensive types of splints. Ambulances normally carry the more expensive splint types as part of their equipment, but this invention envisions use by non-ambulance types such as highway patrols, ski patrols, fire departments, emergency rooms at sporting events and other first responder people. The whole idea is to supply every responder in the field with an inexpensive piece of equipment.

The existing traction splints, the Hare, Thomas and other known types are quite expensive, and beyond the budget possibilities of the organizations or units where they are most needed. Also, they are large, and cannot very conveniently be carried as needed. So, the ability to take immediate care of an injured person with a femur break does not exist with highway patrol cruisers, sporting events, schools, etc. The military is especially in need of a splint such as this.

The splint can be made available for all of the first responder types of units, it representing a manufacturing cost of something in the order of one dollar.

It may be conveniently carried in flat disassembled configuration by a medical man in his bag or automobile or by a paramedic crew in its ambulance or as first aid equipment and may be quickly and conveniently erected at the site of an accident by appropriate folding, and cutting, if indicated, into a suitable configuration for use in immobilizing such as a broken femur or a hip dislocation.

Another key consideration in the invention is that it is of such material, nonmetallic, as to allow its use in connection with X-ray equipment.

The characteristic features which I consider to be novel with my invention, as to its construction and organization and as to its methods of manufacture and operation, will be better understood from a consideration of the following detailed description forming a part of this specification, when read in conjunction with the illustrations in the accompanying drawings, wherein like characters of reference are employed to designate like or corresponding parts throughout the several views and in which.

Figure 1:
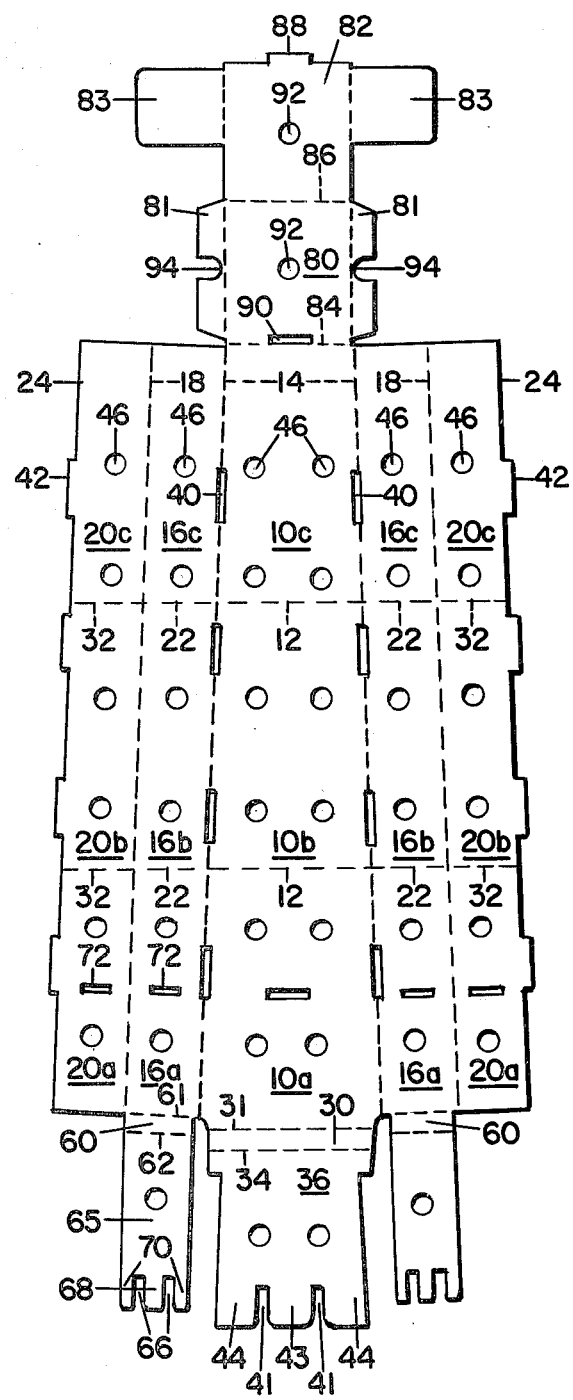
FIG. 1 is a view in top plan of the splint constructed according to a preferred embodiment of the invention and showing the primary construction in fully-opened or expanded-prior-to-erection position.

The splint and traction device according to the preferred embodiments of the invention is formed from a corrugated cardboard or any longitudinally-rifled cardboard so as to increase its stability. As will appear, the folding lines will be softened or marked in fabrication by one of the several pressing treatments generally known in the cardboard industry.

The invention comprises a first elongated base panel which is subdivided into proximal, medial, and distal segments 10a, 10b and 10c respectively, which segments are joinable end-to-end to provide a single first base panel denoted as 10a-10b-10c or are severable along transverse score lines 12 to provide a splint variously consisting of less than the three segments. This feature will be referred to subsequently.

First base panel 10a-10b-10c is provided with laterally-spaced parallel and longitudinally extending first scored fold lines 14, 14 along its opposite side edges.

Areas on each side of the first base panel and outboard of the respective fold lines 14, 14 constitute first side walls 16a, 16b and 16c respectively and their outboard edges are defined by longitudinally-extending second scored fold lines 18 which are laterally-spaced from and parallel to respective first scored fold lines 14.

Areas on each side of the first side walls and outboard thereof constitute second side walls 20a, 20b and 20c respectively and their outboard edges are defined by longitudinally-extending outermost edges 24 which are laterally spaced from and parallel to respective first and second scored fold lines 14 and 18.

That is, the areas on each side of the first base panel and defined by the first and second scored fold lines constitute the first side walls 16a-16b-16c, same being bounded by outboard second scored fold lines 18 and subdivided by transverse score lines 22, which are in reality extensions of score lines 12, and the areas on each side of the first base panel and outboard of the respective first side wall are defined as the second side walls 20a-20b-20c, same being subdivided by transverse score lines 32, which are in reality extensions of score lines 12 and 22.

Second fold line 18 defines the outer edge of the respective first side wall and outboard edge 24 defines the outer edge of the respective second side wall.

Fold lines 14 and 18 allow the creasing of the upper portion of the stock so as to achieve the ready pivotal movement. The first side walls may be pivoted upwardly and inwardly into upright positions in planes normal to the plane of the first base panel and the second side walls may be pivoted into inverted upright positions normal to the plane of the first base panel, with the respective first and second walls being juxtaposed in front-to-front confrontation with each other when fully erected.

Through slots 40 are provided in spaced relationship along first fold lines 14 and tabs 42 are provided in complemental spaced relationship along outer edge 24 so that, in the splint-erected position, a tab 42 may be nestably received within its corresponding slot 40 to aid in the maintenance of the erected position in the well-known manner.

First base panel 10a-10b-10c, first sidewalls 16a-16b-16c and second sidewalls 20a-20b-20c, are provided with rows of aligned through openings 46. The openings in each confronting first and second side wall in the erected condition define a coaxial opening through the side walls so that a cravat c (see FIGS. 3, 4, 5, 6, 7, 9 and 10) may be readily extended in a sinuous threading manner through one pair of side walls and through transversely aligned openings in the first base and through the opposite pair of side walls, for purposes subsequently to appear.

Figure 2:
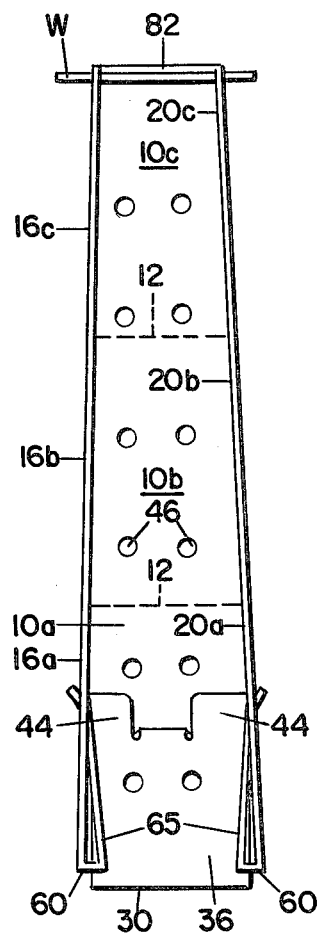
FIG. 2 is a view in top plan showing the FIG. 1 splint in erected position.
Figure 3:
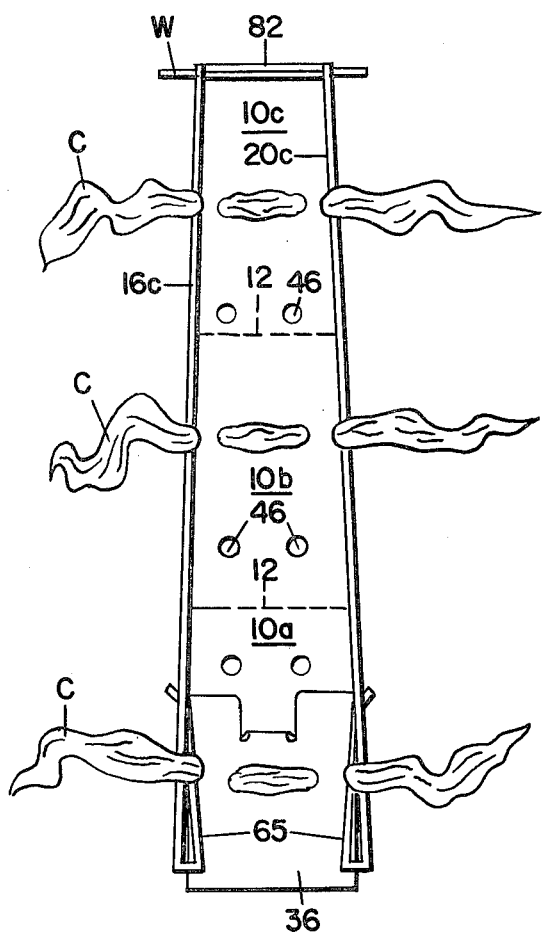
FIG. 3 is a view similar to FIG. 2 showing the cravats in assembled ready-for-use position.
Figure 4:
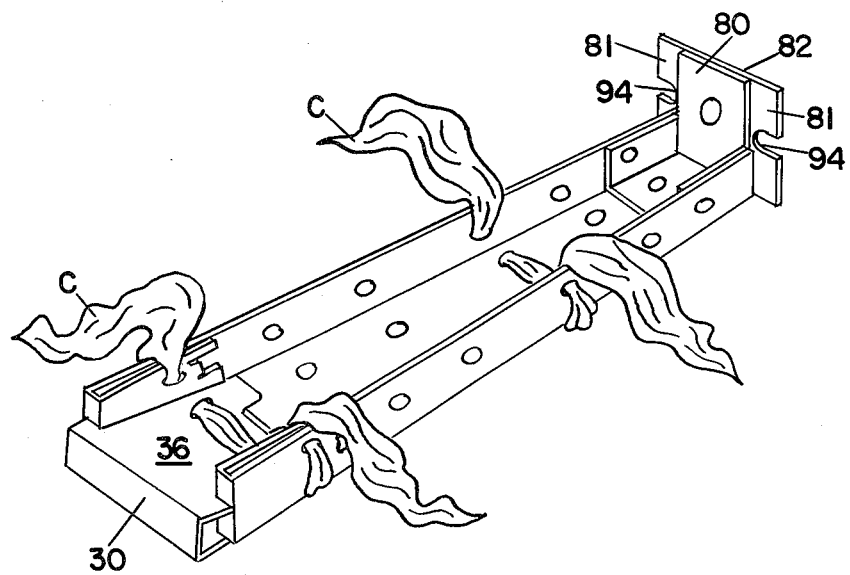
FIG. 4 is an isometric view of the erected splint and showing a third constraining panel member which is formed separately from the other portions of the splint so as to be readily adjustable relative thereto.
Figure 5:
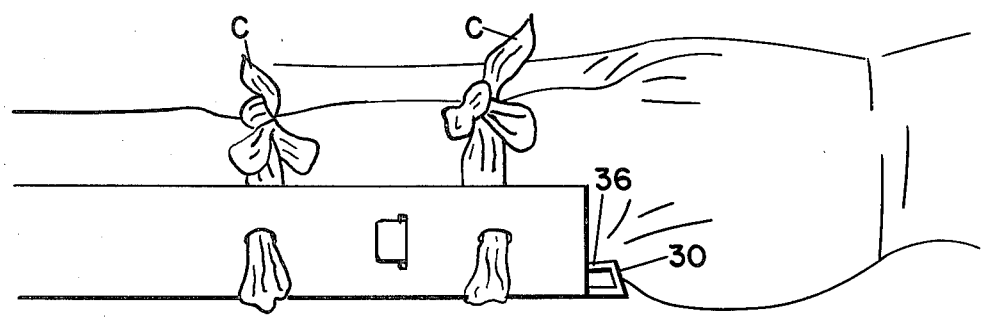
FIG. 5 is a fragmentary view in side elevation of the splint in acutal usage in a manner to exploit the bearing support of the splint against the patient's perineum.

At the inboard end of proximal segment 10a of the first base panel member, a second elevating panel member is integral therewith and is defined by an elevator 30 which is separated from first panel member 10 by a transverse score line 31 and by another transverse score line 34 spaced from and outboard of score line 31, and is further defined by a support panel 36 so related that upon erection elevator 30 can be raised and support panel 36 can be folded along score line 34 so as to be brought into an overlying inclined position returnably over onto the first base panel member, a position best shown in FIG. 2.

Elevator 30 is the element which engages the ischium and is not disposed, upon erecting, at the true vertical. Rather it is disposed at a slight angle, leaning toward the distal end, so as to more closely follow the contour of the patient's rump. Further, it helps to throw the patient's weight forwardly.

The outboard free end of support panel 36 is provided with a pair of spaced inwardly-extending slots 41, 41 so as to define a central tongue 43 and a pair of opposite shoulders 44.

The floor of the first base panel member is slotted at 46 so as to accommodate receipt therethrough of central tongue 43 with opposite shoulders 44 being brought to rest upon the upper surface of the first base panel member. Shifting or shucking of the second elevating panel member relative to the first base panel member is limited by central tongue 43 being fully extended through slot 46 as allowed by slots 41 on opposite sides of the tongue.

The aforementioned angle of disposition of elevator 30, the element which embraces the patient's ischium, is such as to more closely follow the patient's rump and is such as to cause the weight of that body section forwardly so as to more securely lock tongue in its accommodating slot 46.

Elevator 30 is the element which engages the ischium and is not disposed, upon erecting at the true vertical. Rather it is disposed at a slight angle, leaning toward the distal end.

The outboard free end of support panel 36 is provided with a pair of spaced inwardly-extending slots 41, 41 so as to define a central tongue 43 and a pair of opposite shoulders 44.

The floor of the first base panel member is slotted at 46 so as to accommodate receipt therethrough of central tongue 43 with opposite shoulders 44 being brought to rest upon the upper surface of the first base panel member. Shifting or shucking of the second elevating panel member relative to the first base panel member is limited by central tongue 43 being fully extended through slot 46 as allowed by slots 41 on opposite sides of the tongue.

The aforementioned angle of disposition of elevator 30, the element which embraces the patient's ischium, is such as to more closely follow the patient's rump and is such as to cause the weight of that body section forwardly so as to more securely lock tongue in its accommodating slot 46.

At the inboard end each first side wall 16a, a second elevating panel member is integral therewith and is defined by an elevator 60 which is separated from the first side wall by a transverse score line 61 and by another transverse score line 62 spaced from and outboard of score line 61, and is further defined by a support panel 65.

The outboard free end of each support panel 65 is provided with a pair of spaced inwardly-extending slots 66 so as to define a central tongue 68 and a pair of opposite shoulders 70.

The first side walls 16a, 16b and 16c and the second side walls 20a, 20b and 20c are provided with transversely aligned slots 72 so that when the elevator 60 and support panel 65 are erected, simultaneously with the erection of the first and second side walls, to a plane normal to the horizontal plane of the first base panel member, the respective support panels 65 can be folded inwardly along score lines 62 so as to be brought returnably into an overlying position with respect to the respective second wall 20a and the tongue 68 can be engaged in slot 72 to assume the position best shown in FIG. 2.

At the opposite end of the first base panel member 10 is provided a third constraining panel member consisting of an inner third panel part 80 and an outer third panel part 82 foldable as to each other and as to the first base panel member along spaced transverse fold lines 84 and 86 respectively.

A tab 88 on the outer end of outer third panel part 82 is receivable in a complemental slot 90 provided along fold line 86 when the third panel parts are folded into confrontation with each other and the third constraining panel member is folded upwardly and inwardly into vertically erected position relative to the first base panel member as shown in FIG. 2.

Inner and outer third panel parts 80 and 82 are provided with strengthening tabs 81 and 83 respectively as defined by score lines 91 and will further be provided with centrally located complemental through openings 92 which will align with each other when the parts are erected into the back-to-back positions of confrontation.

Figure 6:
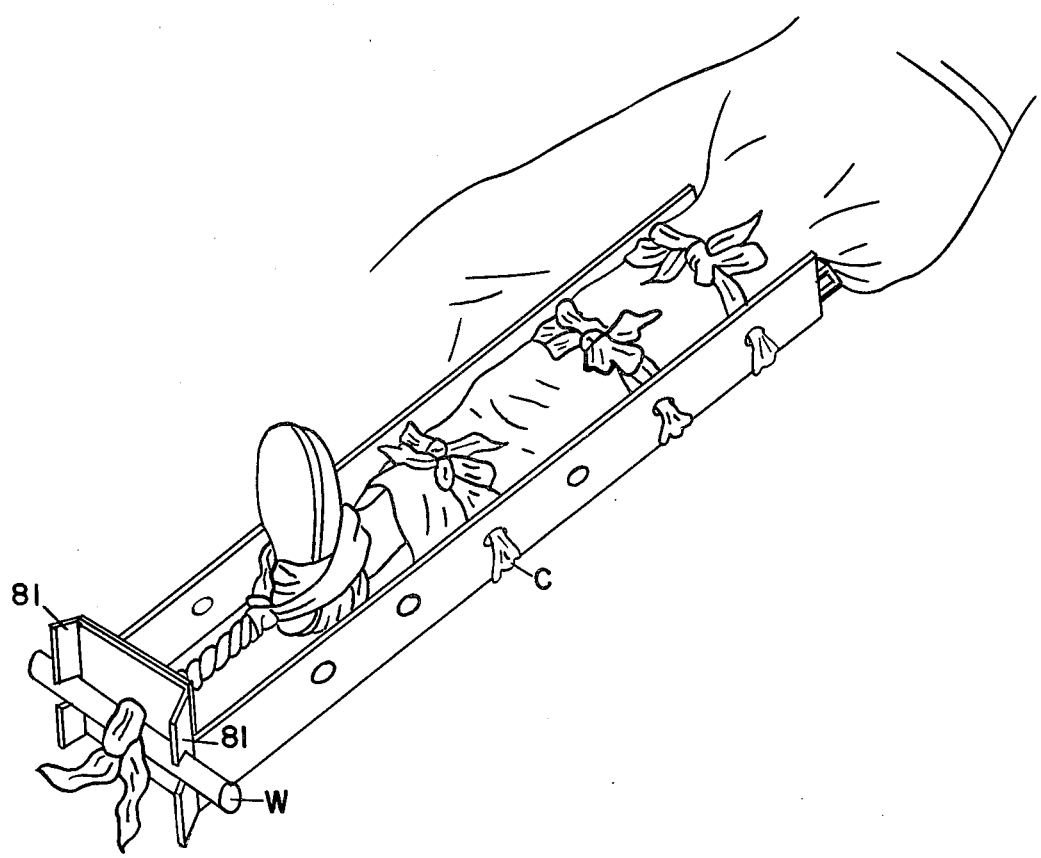
FIG. 6 is a fragmentary isometric view showing the splint in usage for immobilizing and exerting traction on an injured leg.

Tabs 81 are provided with centrally located inwardly-extending windlass notches 94 which will be facing each other upon erection so that, as shown in FIG. 6, a windlass W can be extended thereacross and a cravat C can be engaged with the victim's foot, with the free ends of the cravat being extended through the aligned openings 92, and tied around the windlass so as to maintain a steady longitudinal traction upon the leg.

For thigh and leg fractures, the application of a slow and steady pull to relax the muscles and not produce irritation is recommended therapy. The pull should be gentle and steady in the long axis of the extremity so as to bring the fragment which can be controlled into alignment with the fragment which cannot. Chance for injury to soft tissue and blood vessels is reduced and relief from pain is accomplished in this manner.

For example, if it were desired to place the leg in traction, the leg would first be placed in the splint and bound relatively loosely to the foot piece. During this operation, the perineum piece would be set in place. This method of applying traction is essentially self-contained, in that neither the splint nor the patient need be separately anchored. The external line of stabilizing force runs from the foot piece through the splint segments to the perineum piece which is firmly anchored against the patient's body. The internal line of stabilizing force is from the foot piece through the leg bones and into the body. Inasmuch as the common end points for each line of force are the foot piece and the body, there is no resultant force which tends to move either the splint or the patient. Thus, particularly when the limb is under traction, the splint acts as though it were a part of the patient's body and moves with the body, with no relative motion between the limb and the splint.

Figure 7:
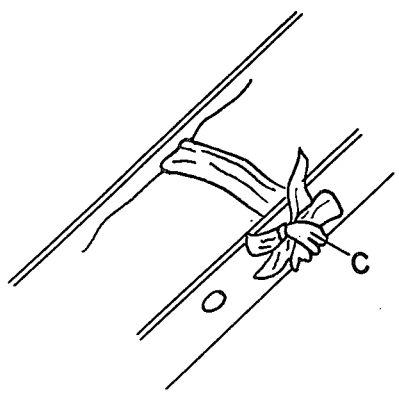
FIG. 7 is a fragmentary isometric view showing the use of a cravat so tied that the knot thereof is on the outboard side area of the splint thereby avoiding placement of the knot over the injury.

As shown in FIG. 7, the cravats can be so tied that the knots thereof are disposed on the outboard side of the splint so as first not to interfere with the victim's other leg and second to keep the knot away from the possibility of aggravating any sensitive or injured part of the leg by tying directly over it.

It is to be explained that the first and second side walls may be broken along any corresponding pairs of score lines 22, 32 so as to allow the bending of the base panel along the score line 12 separating the proximal and medial segments or the medial and distal segments, all to allow the accommodation of the different parts of the base panel to the particular injured limb being served by the angularization of different segments or sections as to each other.

Further, the base panel and side walls can be fully severed along respective score lines 12, 22, and 32 so as to allow the foreshortening of the splint by the elimination of the proximal, or medial, or distal segment for any particular problem.

That is, the segments or sections may be selectively positionable as to each other along the splint length or certain of the segments may be eliminated for a particular usage, thus permitting a wide range of size adjustability. For instance, in the event that an injured adult leg is to be treated, the splint would be assembled using all segments or sections. In the case of a child's leg, it might be desirable to use only the distal and medial segments or the proximal and medial segments. For pediatric injuries, the distal segment alone may be used.

For these purposes, one segment can be nestably received within another segment and the two segments can be held fast to each other as by cravats extended through aligned apertures.

Because of the relatively large interfacing surfaces of the segments, the modified splint will be very stable longitudinally, particularly when the injured limb is under traction.

Figure 8:
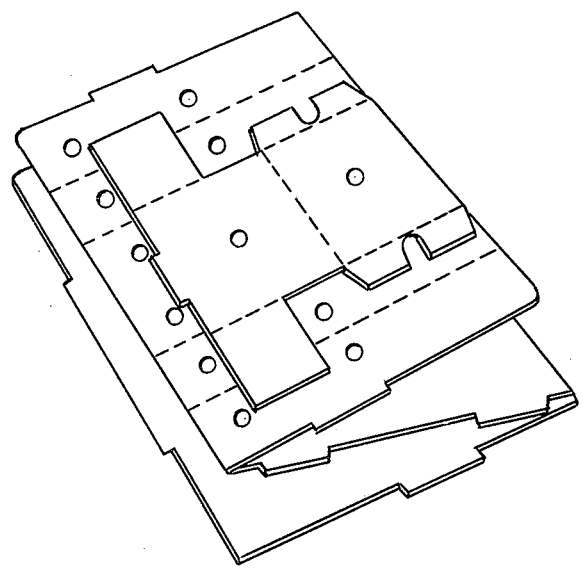
FIG. 8 is an isometric view of the structure of the invention in a partially-collapsed condition.
Figure 9:
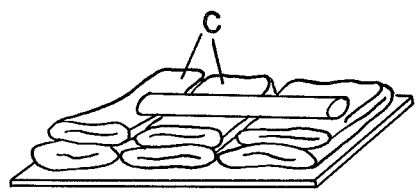
FIG. 9 is an isometric view of the cravats and windless in assembled position for packaging.
Figure 10:
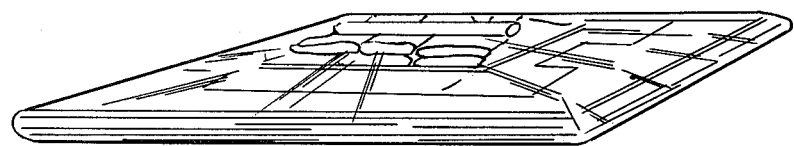
FIG. 10 is an isometric view of the structure of the invention in a fully-collapsed condition.

By the judicious manifolding of the nonerected splint along transverse score lines 12, it may be compactly folded into a flat condition as shown in FIG. 8, with the cravats and windlass being placed upon a support as shown in FIG. 9 for placement upon the top of the manifolded assemblage as shown in FIG. 10 which combination can then be covered with plastic so as to keep same clean until called upon for usage.

I claim:
1. A temporary splint for stabilizing and holding traction on a person's injured leg comprising:
   a first part having a first base panel with integrally-formed laterally-opposite first side panels at the sides of the first panel and adapted for foldable articulation along the side edges of the first base panel and with an integrally-formed first end panel at one end of the first base panel and adapted for foldable articulation along the one end of the first base panel,
   the first base and side and end panels of the first part having interengageable locking formations for defining a generally channel-like leg-accommodating configuration,
   a second part having a second base panel with integrally-formed laterally-opposite second side panels at the sides of the second base panel and adapted for foldable articulation along the side edges of the second base panel and with an integrally-formed second end panel at one end of the second base panel and adapted for foldable articulation along the one end of the second base panel,
   the second base and side and end panels of the second part having interengageable locking formations for defining a generally channel-like leg-accommodating configuration, the first and second parts being nestable in a predetermined telescoping relationship with the first and second end panels disposed at the longitudinally opposite ends of the assemblage and being selectively positioned as to each other for the accommodation of a leg of a particular length, a plurality of tie means, a plurality of spaced transversely-disposed sets of apertures in the telescoped first and second parts for the sinuous entrainment through each set of a tie means in the preclusion of movements of the first and second parts relative to each other and of the accommodated leg relative to the splint, and windlass means interengageable with the second end panel of the second part for the twisting of one of the tie means tied to the leg in the application of a desired traction thereupon.

2. In the temporary splint of claim 1, including the jointure of the first end panel and first base panel being defined by a pair of longitudinally-spaced transversely-extending fold lines whereby the first end panel may be folded into an overlying position upon the first base panel with the space between the fold lines providing a vertically-extending ischium-embracing component delineating a pressure plate for accommodating to the patient's body region adjacent the injury.

3. A collapsible temporary splint for ready erection and service in holding traction on a person's injured leg comprising in combination:

a base panel, a pair of side panels integrally formed with the base panel at the laterally opposite sides thereof and adaptable for foldable articulation relative thereto, a first end panel integrally formed with the base panel at one end thereof and adaptable for foldable articulation relative thereto along fold lines spaced from each other whereby the first end panel may be folded into overlying position upon the base panel with the space between the fold lines providing a vertically-extending ischium-embracing component for accommodating to the patient's body region adjacent the femur, a second end panel integrally formed with the base panel at the opposite end thereof and adaptable for foldable articulation relative thereto, the base and side and first end and second end panels having interengageable locking formations for defining a channel-like leg-accommodating configuration upon erection, a plurality of tie means, a plurality of spaced transversely-disposed sets of apertures in the base and side panels for the sinuous entrainment through each set of a tie means in the preclusion of movement of the accommodated leg relative to the splint, windlass means interengageable with the second end panel for the twisting of one of the tie means tied to the accommodated leg in the application of a desired traction thereupon.

4. A disposable splint for the temporary support of a fractured leg of a patient which may be carried to the accident scene in a collapsed condition and erected thereat to a leg-supporting condition, the splint including:

a first part having a first base panel with integrally-formed laterally-opposite first side panels at the sides of the first panel and adapted for foldable articulation along the side edges of the first base panel and with an integrally-formed first end panel at one end of the first base panel and adapted for foldable articulation along the said one end of the first base panel, the first base and side and end panels for the first part having interengageable locking formations for defining a generally channel-like leg-accommodating configuration, the jointure of the first end panel and first base panel of the first part being defined by a pair of longitudinally-spaced transversely-extending fold lines whereby the first end panel may be folded into an overlying position upon the first base panel with the space between the fold lines providing a vertically-extending ischium-embracing pillow at the said one end for accommodating to the patient's body region adjacent the injured leg, a second part having a second base panel with integrally-formed laterally-opposite second side panels at the sides of the second base panel and adapted for foldable articulation along the side edges of the second base panel and with an integrally-formed second end panel at one end of the second base panel and adapted for foldable articulation along the one end of the second base panel, the second base and side and end panels of the second part having interengageable locking formations for defining a generally channel-like leg-accommodating configuration, the first and second parts being nestable in a predetermined telescoping relationship with the first and second end panels disposed at the longitudinally opposite ends of the assemblage and being selectively positioned as to each other for the accommodation of a leg of a particular length, a plurality of tie means, a plurality of spaced and aligned transversely-disposed sets of apertures in the telescoped first and second parts for the sinuous entrainment of a tie means through each set in the preclusion of relative movements of the first and second parts and of the accommodated leg relative to the splint, windlass means including a traction cord for securement to the leg and interengagement with the second end panel in applying a proper tension upon the leg.

* * * * *